(12) United States Patent
Lenzenhuber et al.

(10) Patent No.: US 12,362,063 B2
(45) Date of Patent: Jul. 15, 2025

(54) METHOD FOR CAPTURING AND DOCUMENTING A WORK CYCLE OF STERILIZABLE MEDICAL PRODUCT

(71) Applicant: Aesculap AG, Tuttlingen (DE)

(72) Inventors: Frederick Lenzenhuber, Tuttlingen (DE); Tanja Hahn, Immendingen/Zimmern (DE); Gerhard Faller, Braeunlingen (DE)

(73) Assignee: Aesculap AG, Tuttlingen (DE)

( * ) Notice: Subject to any disclaimer, the term of this patent is extended or adjusted under 35 U.S.C. 154(b) by 122 days.

(21) Appl. No.: 18/283,567

(22) PCT Filed: Mar. 17, 2022

(86) PCT No.: PCT/EP2022/056948
§ 371 (c)(1),
(2) Date: Sep. 22, 2023

(87) PCT Pub. No.: WO2022/200160
PCT Pub. Date: Sep. 29, 2022

(65) Prior Publication Data
US 2024/0170140 A1    May 23, 2024

(30) Foreign Application Priority Data

Mar. 24, 2021 (DE) ..................... 10 2021 107 405.3

(51) Int. Cl.
*G16H 40/40* (2018.01)
*A61B 90/50* (2016.01)
(Continued)

(52) U.S. Cl.
CPC ............. *G16H 40/40* (2018.01); *A61B 90/50* (2016.02); *A61B 90/70* (2016.02); *A61B 90/98* (2016.02);
(Continued)

(58) Field of Classification Search
CPC ........ G16H 40/40; G16H 40/20; A61B 90/50; A61B 90/70; A61B 90/98; A61B 2090/0803; A61B 90/94; A61L 2/28
See application file for complete search history.

(56) References Cited

U.S. PATENT DOCUMENTS

| 4,444,596 A | 4/1984 | Gortz et al. |
| 5,380,369 A | 1/1995 | Steinhauser et al. |

(Continued)

FOREIGN PATENT DOCUMENTS

| CN | 107427301 A | 12/2017 |
| CN | 107708599 A | 2/2018 |

(Continued)

OTHER PUBLICATIONS

Figeroa, Santiago et al. "An Attribute-Based Access Control Model in RFID Systems Based on Blockchain Decentralized Applications for Healthcare Environments." Computers 2019, 8(3), 57; Submission received: Jun. 13, 2019 / Revised: Jul. 19, 2019 / Accepted: Jul. 2019 / Published: Jul. 31, 2019. (Year: 2019).*

(Continued)

*Primary Examiner* — Linh Giang Le
(74) *Attorney, Agent, or Firm* — Christopher A. Rothe; CM Law

(57) ABSTRACT

A method includes steps for capturing and documenting a work cycle of a sterilizable medical product which is preferably held in a holding apparatus and which communicates, preferably wirelessly, with an external data-processing device, which is preferably disposed in the holding and/or storing apparatus. First, a process step or the performance of a process step of the work cycle is captured in accordance with an output signal of at least one sensor preferably disposed in the holding and/or storing apparatus. The output signal is processed further by the data-processing device to form cycle information. The cycle information is stored in a (Continued)

data chain/data sequence saved in a data memory of the medical product. The cycle information is stored by exactly one bit in the data chain.

10 Claims, 1 Drawing Sheet

(51) Int. Cl.
*A61B 90/70* (2016.01)
*A61B 90/98* (2016.01)
*A61L 2/28* (2006.01)
*G16H 40/20* (2018.01)
*A61B 90/00* (2016.01)

(52) U.S. Cl.
CPC .............. *A61L 2/28* (2013.01); *G16H 40/20* (2018.01); *A61B 2090/0803* (2016.02)

(56) References Cited

U.S. PATENT DOCUMENTS

| | | | |
|---|---|---|---|
| 5,432,863 A * | 7/1995 | Benati | G06V 40/193 382/167 |
| 9,101,337 B2 | 8/2015 | Hoegerle et al. | |
| 10,368,958 B2 | 8/2019 | Wehrle et al. | |
| 2004/0209223 A1 | 10/2004 | Beier et al. | |
| 2008/0130706 A1 | 6/2008 | Kellner et al. | |
| 2009/0128330 A1 | 5/2009 | Monroe | |
| 2009/0261549 A1 | 10/2009 | Kral | |
| 2016/0291998 A1* | 10/2016 | Dong | G06F 3/0683 |
| 2017/0277864 A1 | 9/2017 | Bassion et al. | |
| 2018/0052454 A1 | 2/2018 | Magno et al. | |
| 2018/0153639 A1 | 6/2018 | Wehrle et al. | |
| 2018/0228341 A1 | 8/2018 | Stojalowski | |
| 2018/0353275 A1 | 12/2018 | St. Louis et al. | |
| 2022/0008155 A1 | 1/2022 | Högerle et al. | |

FOREIGN PATENT DOCUMENTS

| | | | |
|---|---|---|---|
| DE | 102009051619 A1 | 5/2011 | |
| DE | 102010017624 A1 | 12/2011 | |
| DE | 102011050192 A1 | 11/2012 | |
| DE | 102015108264 A1 | 12/2016 | |
| DE | 102018126969 A1 | 4/2020 | |
| EP | 2514386 A1 | 10/2012 | |
| JP | 2009136492 A | 6/2009 | |
| JP | 2009172013 A | 8/2009 | |
| JP | 2017205358 A | 11/2017 | |
| KR | 101909009 B1 | 10/2018 | |
| WO | 03092524 A1 | 11/2003 | |
| WO | 2008020770 A1 | 2/2008 | |
| WO | WO-2020249276 A1 * | 12/2020 | ............... A61L 2/07 |

OTHER PUBLICATIONS

International Search Report received in Application No. PCT/EP2019/079342 dated Feb. 13, 2020, with translation, 7 pages.
Office Action received in Chinese Application No. 201980069835.3 dated Sep. 28, 2023, with translation, 13 pages.
Office Action received in Japanese Application No. 2021-523082 dated Jun. 14, 2023, with translation, 22 pages.
Search Report received in German Application No. 10 2018 126 969.2 dated Aug. 20, 2019, with translation, 20 pages.
TPC Advanced Technology, "H6000, 6005 & 6025 Handpiece Cleaning and Lubrication System User Manual," available online Jun. 22, 2012 (Year: 2012).
Written Opinion received in Application No. PCT/EP2019/079342 dated Feb. 13, 2020, with translation, 11 pages.
Search Report received in German Application No. 10 2021 107 405.3 dated Jun. 9, 2021, with translation, 16 pages.
Search Report received in International Application No. PCT/EP2022/056948 dated Jul. 19, 2022, with translation, 5 pages.
Written Opinion received in International Application No. PCT/EP2022/056948 dated Jul. 19, 2022, with translation, 13 pages.

* cited by examiner

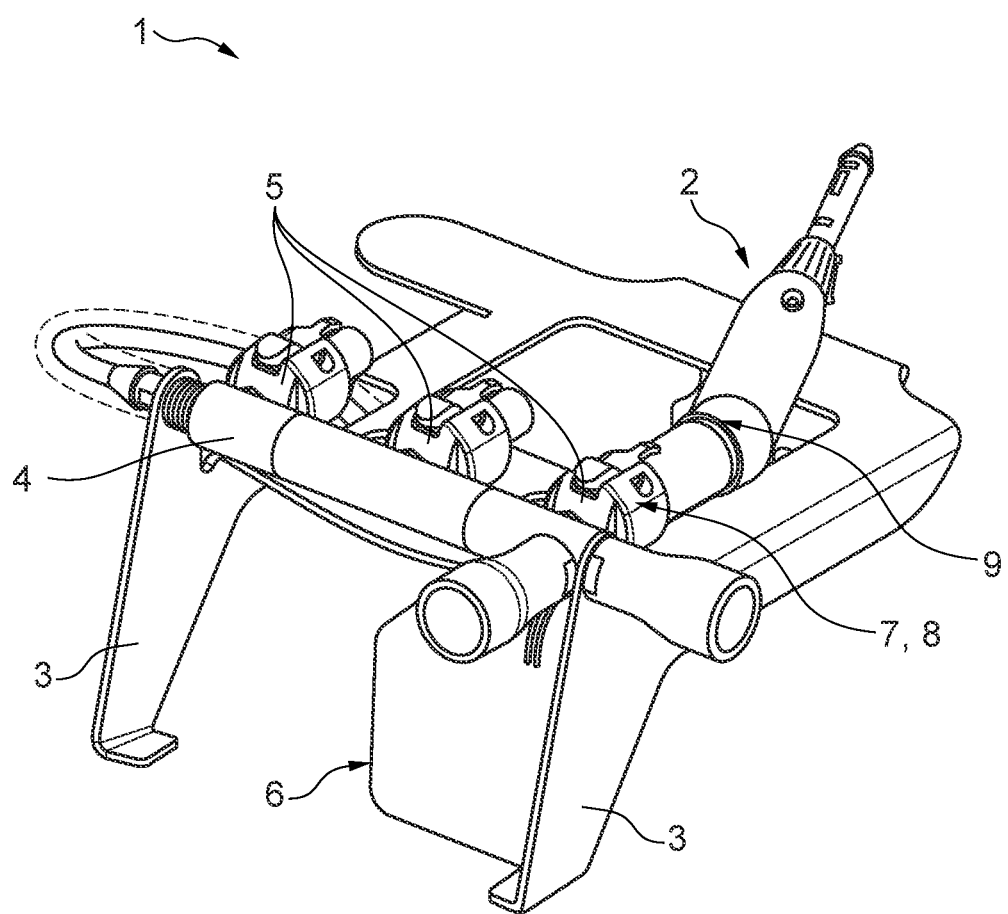

METHOD FOR CAPTURING AND DOCUMENTING A WORK CYCLE OF STERILIZABLE MEDICAL PRODUCT

CROSS-REFERENCE TO RELATED APPLICATION(S)

This application is the United States national stage entry of International Application No. PCT/EP2022/056948, filed Mar. 17, 2022, and claims priority to German Application No. 10 2021 107 405.3, filed Mar. 24, 2021. The contents of International Application No. PCT/EP2022/056948 and German Application No. 10 2021 107 405.3 are incorporated by reference herein in their entireties.

FIELD

The disclosure relates to a method for detecting and documenting a work cycle of a cleanable/sterilizable medical product, in particular a handpiece, preferably held in a holding/rinsing and/or storing device, in particular a holder for motor systems or other systems as well as a sieve, wherein the medical product communicates, preferably wirelessly, with an external data-processing device, preferably arranged in the holding device or connected thereto. For this purpose, first an individual process step or the performance of each individual process step of the work cycle is detected as a function of an output signal of at least one sensor, preferably arranged in the holding device, before the output signal is (further) processed by the data-processing device to form cycle information and this cycle information is finally stored in a data chain/data sequence stored in a data memory of the medical product.

BACKGROUND

In most cases, the detection of the sterile goods cycle for medical instruments and tools is based on written documenting or checks at the end of the reprocessing cycle. The problem is that it is not possible to say with certainty whether and how the individual process steps of the sterile goods cycle, such as pre-cleaning, cleaning and disinfection, maintenance and sterilization, were carried out. Valid data are generated by handwritten records, but this procedure is time-consuming and highly error-prone. Furthermore, operating times of electrical, pneumatic or hydraulic products cannot be documented in relation to the respective tool or product, i.e. not at individual product level. Another problem is the lack of identification of individual instruments and tools as well as the detection and determination of their service life or their traceability.

For monitoring and traceability of sterile goods, it has to be possible to determine whether medical technology instruments or devices have successfully undergone the entire reprocessing process and whether all the necessary maintenance or process steps have been carried out. The problem is that sensors can only be housed in larger devices and there is in particular no possibility of monitoring for instruments that are not current-regulated.

For this reason, special holding devices are usually used for cleaning and holding motors and/or handpieces of surgical instruments (as is also the case in the present disclosure). Such a holding device is described, inter alia, in DE 10 2010 017 624. The holders are arranged with medical products arranged in the holding devices in medical cleanings plants, in particular sterilizers, rinsing plants or the like. In addition, it is also possible for the holders to be used together with sterile containers and to be arranged within them, so that after sterilization of the medical products it is ensured that renewed contamination of the medical products is effectively prevented.

It is also common practice, for example, for reusable implants to be reprocessed in a similar way to the surgical instruments mentioned. In the case of a large number of these reprocessable implants, especially if they are made of titanium, frequent reprocessing leads to quality losses in the medical product. In the case of titanium screws, for example, the thickness of the oxide layer protecting the titanium screw from corrosion and biofilm formation is reduced by the frequent use of aggressive cleaning substances. Reprocessable implants often come in sets which, regardless of whether individual elements of the set are actually used, always undergo a reprocessing process together.

However, it is thus currently not possible to count product-related (completely and correctly performed) reprocessing cycles and to detect, document and draw relevant conclusions from this information. In other words, automated documenting of reprocessing cycles over the entire life of a tool or product at individual product level is currently unknown.

A reprocessing cycle essentially comprises a manual pre-cleaning step and/or a mechanical pre-cleaning in an ultrasonic bath, a cleaning step in the washer disinfector (WD), if necessary a maintenance step such as oiling, and a sterilization step.

Due to the lack of information regarding (correctly) performed cycles, statements cannot be made regarding the following points either:
  general condition
  service life/end of service life
  maintenance interval
  performance and suitability for subsequent operation (as described in the purpose statement)
  reduced maintenance of product and product damage, if any
  temperature overshoots and undershoots and, if applicable, product damage In the future, issues relating to tracking, traceability and lifecycle management will become increasingly important, as will the provision of evidence in the event of complaints. As mentioned above, hospitals therefore spend a considerable amount of time and effort manually detecting this information and documenting it in databases.

At present, a user or customer cannot directly recognize how often a product or tool has been (correctly) reprocessed and whether there are deficits or irregularities in the (reprocessing) process or whether maintenance may be necessary. Up to now, the products therefore have to be subjected to a defined maintenance interval, even if this might not be necessary due to the product condition In order to be able to track how often a medical product, for example the handpiece, has been (correctly) reprocessed during its service life, it is known, for example, to provide integrated temperature sensors with independent energy supply units or energy harvesting units in a motor of the medical product, which detect the temperature during the reprocessing/cleaning process and store it in a data memory of the motor. A motor with suitable storage devices for this purpose is described, for example, in DE 10 2011 050 192. A particular disadvantage of such a solution is that it takes up a relatively large amount of installation space in the medical product and increases its weight. These disadvantages are unacceptable in particular for medical products used in neurosurgery, minimally invasive procedures or similar procedures.

Furthermore, DE 10 2018 126 969 A1 shows a holding device for holding at least one sterilizable medical product, in particular during a cleaning process and for storing the medical product before and/or after the cleaning process. The holding device has a data-processing device that is connected/connectable to at least one sensor in a signal-conducting manner, the sensor being in particular a temperature sensor for determining a temperature during the cleaning process and/or a pressure sensor for determining a static and/or dynamic pressure of a cleaning liquid during the cleaning process. The data-processing device processes the sensor signals into cleaning information.

Furthermore, the data-processing device may be connected/connectable to a data memory of the medical product so that the cleaning information is stored in the data memory. I.e. the data-processing device can write the determined cleaning information into the data memory of the medical product.

In other words, the holding device or product detection system of DE 10 2018 126 969 A1 makes it possible to count the reprocessing cycles for all products in combination with individualized storage and to save this information in the product itself. In particular, it can also be viewed whether all individual process steps have been observed and carried out. As mentioned above, the number of reprocessing cycles is a proportional measure of the general condition, the service life or end of service life, a maintenance interval, the performance and suitability for a follow-up operation, inadequate care of the product and any resulting product damage, as well as temperature overshoots and undershoots and product damage.

This means that with previous solutions for documenting the sterile goods cycle, a great deal of manual effort is required. When packing the products or tools in the reprocessing unit for medical products (AEMP), the products often have to be inspected (item number and serial number) and are then imported into software. This is a manual, error-prone, labor-intensive and time-consuming handling process.

A first step towards optimized detection of sterile goods cycles is the known detection of barcodes, data matrix codes or RFID chips. Sometimes, however, this still requires a manual work step, such as scanning with additional (reading) devices. Under certain circumstances, this can only take place at one point in the sterile goods cycle/sterilization goods cycle, which only provides a selective insight into the process.

However, with previous solutions, no data that are service-life relevant are written to the data memory. Often, only the unique ID (UID) of the chip is used to establish a connection ('bridge') into the management software and thus to create a link.

SUMMARY

It is the objects and objectives of the disclosure to eliminate or at least reduce the disadvantages of the prior art. In particular, a method for detecting a sterile goods cycle is to be provided, which enables a product-related, i.e. related to individual product level (e.g. in connection with a LOT number, serial number or Global Trade Item Number (GTIN)), documenting of an entire work cycle/reprocessing cycle/sterile goods cycle, preferably over the entire product service life, and thus improves tracking, traceability and service life management.

In other words, the disclosure is intended to ensure that the relevant individual steps/process steps of a work cycle can be written directly to an internal data memory of the medical product despite very limited storage capacities.

The method according to the present disclosure is therefore configured in such a way that the/each individual cycle information/cleaning information is stored/recorded with exactly one (data) bit (i.e. binary coded) in the data chain. In other words, each cycle information related to a single cycle process step is stored as binary data in the data memory of the medical product. In yet other words, the cycle information for the individual process steps of the work cycle is stored as a sequence/order of binary data. Each position, i.e. each bit, in the data chain essentially corresponds to a single process step or work cycle operation. The position in the data chain thus determines the type of process step, whereas the value of the binary data or bit provides information about the successful performance of the process step. According to the disclosure, storing the cycle information as a sequence of binary data thus has a direct influence on the (physical) size of the data memory/storage medium or on the number of cycles that can be stored with a given storage medium. If a larger number of work cycles can be stored in a storage medium, the number of manual and error-prone handling steps for product sorting is reduced.

In a preferred variant, the data memory is configured as an RFID chip, in particular an NFC chip, with a housing preferably made of glass. Alternatively, the data memory may also be configured as a UHF or SUHF chip. The data memory thus enables communication with the data-processing device and at the same time provides storage capacity/storage space. In particular, the data memory or RFID chip can operate as a 'single source of truth' (SSOT). This means that each piece of data/data element is processed at just one point, in particular the data-processing device, in order to act as a unique key on the one hand and as a data carrier on the other hand between the individual data detection stations. This ensures that the current data status is always stored on the chip and that this data can be read out at different stations in the process.

In a preferred embodiment, the work cycle may include at least the process steps manual or mechanical pre-cleaning, cleaning and disinfection, maintenance and, if necessary, sterilization of the medical product, as well as working with the medical product (medical/surgical use). As mentioned above, pre-cleaning can be performed manually or mechanically in the form of ultrasonic cleaning, for example in an ultrasonic bath. The process step 'cleaning and disinfection' may be performed, preferably (partially) automated, in a washer disinfector (WD). Furthermore, the maintenance step may include, for example, oiling of the medical product or parts of the medical product. Before the medical product can be used, for example in the context of an operation, the medical product can also be sterilized. In addition, the work cycle may of course include further process steps. For example, a test run can be additionally integrated into the work cycle. The addition of further process steps is possible at this point at any time.

Furthermore, it is advantageous if a plurality of work cycles can be stored in the data memory and a, preferably negated, binary datum is arranged for delimiting successive work cycles. I.e. in order to make clear when a work cycle ends and when a further work cycle following the first work cycle begins, a further (single) bit is used between the two work cycles to store a binary (delimitation) datum. This additional bit (binary datum) is preferably negated, i.e. if, as described in more detail below, a successfully (unsuccessfully) executed process step is stored with '1' (or '0'), a singular '0' or '1' is prefixed as additional (delimitation) date.

According to the invention, the data chain stored in the data memory may further comprise data for identifying the medical product, in particular an item number, serial number, GTIN or further identification characteristics.

Furthermore, it is particularly preferred if the data chain comprises data for defining a structure of the data chain, in particular a protocol version. Such a protocol version can define a structure of the data chain, respectively of the coding of the data chain, i.e. the way of the subsequent arrangement of the bits. If the structure is changed, for example by adding a process step, the protocol version can be used to easily distinguish this structure.

In a preferred further development, the data chain may also comprise data for determining a maintenance interval, in particular a service counter/service meter. The service counter can indicate, for example, how often the medical product has been serviced and how often it has been reset in this context, i.e. how often the data memory has been read out. This makes it easy to prevent subsequent process steps from falsifying the data chain after the data chain has been reset, for example during maintenance or servicing or when the data memory is full.

According to a preferred embodiment, a successfully executed process step may be stored as '1' and an unsuccessfully executed process step is stored as '0'. In addition, a complete work cycle in which all process steps have been performed successfully can be stored as a singular '1', i.e. in a complete work cycle the cycle information of the individual process steps, including the above-mentioned (delimitation) datum, is not stored individually as a sequence/order, but is combined as a singular '1'. Since such a singular '1' requires only one bit, a complete (correct) work cycle can be stored with one bit. Thus, the memory capacity can be used optimally and the number of stored work cycles can be increased easily and efficiently. An alternative embodiment is characterized by the fact that a successfully executed process step may be stored with '0' and an unsuccessfully executed process step with '1'. I.e. in the alternative embodiment, the process steps, or their cycle information, are recorded in negated form. Here, too, it is conceivable and advantageous to store a complete work cycle in which all process steps have been performed successfully, including the (delimitation) date, as a singular '0'.

According to the invention, the at least one sensor may be a temperature sensor for determining a temperature during the work cycle and/or a pressure sensor for determining a static and/or dynamic pressure of a fluid, in particular a cleaning agent.

In other words, according to the invention, a data memory in the form of an RFID chip can be incorporated in the medical products or tools, which is preferably made of glass (as a casting compound or with additional casting compound) ('glass tag') and can be procured in different sizes. In particular, the data memory may have a ferrite core with a copper coil, which is embedded in a glass tube and encapsulated with epoxy resin. A glass cap is applied to the glass tube and (ultrasonically) welded to the glass tube to hermetically seal the glass tube. However, in addition to a glass-enclosed assembly, other materials, such as ceramics, are quite conceivable for enclosing the assembly. This chip, placed at a predetermined position on the medical product, can always be brought into a distinct relative position to an antenna (on the holding device) in combination with a corresponding holding device for the medical product. This allows the electronics to access the data content.

All medical products in a hospital are in the sterile goods cycle and have to pass through this in order to be reprocessed. This sterile goods cycle includes at least one of the following steps:
  pre-cleaning manually or mechanically (ultrasound—'Ultrasonic'—U)
  cleaning and disinfection ('Disinfection'—D)
  maintenance ('Maintain'—M)
  sterilization ('Sterilization'—S)
  working in the operating room ('Work'—W)

The information as to whether a process (step) is complete or incomplete is to be stored in the data memory. As mentioned above, the RFID chip serves as an SSOT, i.e. each data element is processed at only one point in order to act between the individual stations of the data detection on the one hand as a unique key (device+serial number) and on the other hand as a data carrier (number of cycles+cycle success). This ensures that the current data status is always stored on the chip and that this data can be read out at different stations in the process (e.g. for transfer to an external storage medium such as a cloud).

All product-relevant data can also be stored on the data carrier. These are:
  item number
  serial number/manufacturer's serial number or LOT number
  GTIN Preferably, the GTIN may consist of a numerical sequence with 14 digits. It is of particular advantage if the GTIN has a, preferably preceding, filling position, a two-digit, preceding country identifier, a business identification number with 5 to 7 digits, an item number with 3 to 5 digits, and a control digit. In this case, the item number can therefore be integrated into the GTIN.

Furthermore, counter readings are stored for manufacturer-related handling:
  Protocol version: the version defines the structure of the coding, i.e. the way of the subsequent arrangement of the bits. In case of a change of the structure (e.g. addition of a process step) this structure can be distinguished in the processing devices with the help of the version.
  Service counter: this counter reading shows how often the product has already been serviced and how often it has thus been reset. This prevents subsequent process steps from falsifying the sequence after a reset of the sequence (e.g. memory full, service at the manufacturer).

In other words, such a data chain according to the invention is composed as follows:
  item number+serial number+GTIN+protocol version+service counter+cycle count.

The sequence/order of the data stored in the data chain is irrelevant here, i.e. the order can be swapped as required and is defined once. For example, the protocol version can be placed in front and the order can then be mapped via the protocol version.

In addition, it is conceivable that identifiers precede the respective data, i.e. the item number, the serial number, the GTIN, the protocol version and/or the service counter.

In order to describe a reprocessing cycle completely, the process steps (U-D-M-S-W), as mentioned above, are necessary. According to the invention, these are to be saved in binary form in this sequence, where '1' indicates a complete process step and '0' an incomplete process step. In order to have a distinction to preceding work cycles, a '0' can be prefixed, which is deleted at a following conversion.

In other words, the present invention relates to a method/process for logically detecting processing cycles (consisting of several individual process steps) and for storing data on the data carrier with optimum utilization of the finite/limited storage space in order to be able to log/detect a maximum number of cycles. Thus, information can be documented in the product. In addition, documentation of individual steps in the reprocessing cycle and detection of faulty cycles and/or forgotten process steps is possible. Furthermore, transparency can be increased in the event of service, since the data carrier or RFID chip carries all relevant information. In addition, it is possible to determine usage, which in turn results in new business models and an exact indication of the service life of the medical product.

BRIEF DESCRIPTION OF THE DRAWINGS

The disclosure is explained in more detail below with reference to preferred embodiments with the aid of a FIGURE.

The FIGURE shows perspective view of a holding device for holding a medical product according to a preferred embodiment.

The FIGURE is of a schematic nature and serves only for understanding the invention.

DETAILED DESCRIPTION

The FIGURE shows an embodiment of a known cleaning/holding device 1 for holding at least one preferably sterilizable medical product 2 during a cleaning process and for storing the medical product 2 before and after the cleaning process. Alternatively, the holding device 1 may also be a sterile screen. The medical product 2 is arranged in/on the holding device 1 and is held by it in such a way that it cannot change its position relative to the holding device 1 either during the cleaning process or during transport. The holding devices 1 shown are configured in such a way that, if required, they can be arranged inside a sterile container which is not shown here or the sterile container itself represents the storage.

For this purpose, the holding device 1 has a platform-like (grid) frame, for example a sheet metal frame, with support feet 3, to which at least one pipeline 4 is fixed, which has a number of branches 5 along the pipeline 4, which form connection points/connection ports for the hollow medical products 2 such as handpieces. In the area of these connection ports, the (sheet metal) frame defines a recess/depression or clamping jaws for stable support of the respective medical product 2.

The holding device 1 shown also has a data-processing device 6 and at least one temperature sensor 7 for detecting a temperature, which is arranged in the area of the connection ports. The holding device 1 shown in the FIGURE also has at least one pressure sensor 8 for detecting a static pressure of a cleaning liquid, which is also arranged in the area of the connection port.

The temperature sensor 7 and the pressure sensor 8 make it possible to determine whether a process step of a work cycle through which the medical product 2 is passing has been successfully completed. In other words, the data-processing device 6 decides, depending on the output signals of the temperature sensor 7 and the pressure sensor 8, whether the process step has been successfully completed and processes the output signals into (cycle) information.

Furthermore, the medical product 2 is in communication with the data-processing device 6, preferably via a wireless radio link, and also has an internal data memory 9 so that the data-processing device 6 can write the cycle information to the internal data memory 9 of the medical product 2 after processing the output signals. In other words, the information is stored directly in the data memory 9 of the medical product 2. For this purpose, the data memory 9 is configured as an RFID chip in the preferred embodiment. This can communicate wirelessly with the data-processing device 6 and can also store the information.

In other words, according to the invention, the medical product 2 incorporates the data memory 9 in the form of an RFID chip, which is preferably housed in a glass housing ('glass tag') and can be procured in different sizes. However, in addition to a glass assembly, other materials, such as ceramics, are also conceivable for enclosing the assembly.

In combination with the holding device 1, this chip can always be placed in a distinct position with respect to a transmitting device/antenna in order to ensure communication/a radio link between the data-processing device 6 and the medical product 2. Thus, the data-processing device 6 can access the data stored in the medical product 2 and can store information in the data memory 9 of the medical product 2.

As mentioned above, the medical product 2 is held in/on the holding device 1 both during the cleaning process and during transport. In order to work with the medical product 2, it finally needs to be removed from the holding device 1. An entire sequence with all cleaning processes up to a work step (medical/surgical use/application of the product) is referred to below as a 'work cycle'.

Over its service life, the medical product 2 undergoes a large number of work cycles, i.e. the medical product 2 is reprocessed and then the medical product 2 is used before it is reprocessed again. The large number of work cycles is referred to below as the 'sterile goods cycle'.

The medical product 2 is in the work cycle in a medical facility, such as a hospital, and has to pass through this work cycle in order to be reprocessed. This work cycle comprises at least the following steps:
  pre-cleaning manually or mechanically (ultrasound—'Ultrasonic'—U)
  cleaning and disinfection ('Disinfection'—D)
  maintenance ('Maintain'—M)
  Sterilization ('Sterilization'—S)
  Work in the operating room ('Work'—W)

In other words, the medical product 2 is pre-cleaned manually or in an ultrasonic bath in a first process step (process step U). This is followed by cleaning and disinfection (process step D) in a washer disinfector (WD). The medical product 2 is then subjected to a maintenance step (process step M). Here, the medical product 2 may be oiled, for example, before it is finally sterilized in the next process step (process step S). Once this reprocessing cycle has been completed, the medical product 2 can be used in an operation (process step W).

After performing the respective process steps, the data-processing device 6 determines, for example by evaluating the output signals of the sensors 7, 8, whether the respective process step has been successfully/completely performed. Depending on this, the data-processing device 6 stores the information in the data memory 9. In other words, the information as to whether a process step has been completely or incompletely performed is saved in the data memory 9.

In the preferred embodiment, the RFID chip as data memory 9 serves as an SSOT, i.e. each data element is processed at only one point in order to be used between the individual stations of the data detection on the one hand as a unique key (device+serial number or GTIN) and on the other hand as data memory/data carrier 9 (number of cycles+ cycle success). This ensures that the current data status is always stored on the chip, i.e. in the data memory 9, and that this data can be read out at different stations in the work cycle (e.g. for transfer to an external storage medium such as a cloud).

All product-relevant data are stored in the data memory 9 of the medical product 2. These are:
- item number
- serial number/manufacturer's serial number or LOT number
- GTIN In addition to the item number and serial number data required to identify the medical product 2, counter readings are stored for manufacturer-related handling. These are:
- Protocol version: the version defines the structure of the coding, i.e. the way of the subsequent arrangement of the bits. In case of a change of the structure (e.g. addition of a further process step) this structure can be distinguished in the processing devices with the help of the version.
- Service counter: this counter reading shows how often the product has already been serviced and how often it has thus been reset. This prevents subsequent process steps from falsifying the sequence after a reset of the sequence (e.g. memory full, service at the manufacturer).

Thus, a data chain consisting of item number, serial number, protocol version and service counter is stored in the data memory 9, which is extended by a count of the work cycles described in more detail below. Such a data chain can thus look as follows, for example:

GA861 00001345 001 000+count of work cycles

'GA861' describes the item number, '00001345' the serial number, '001' the protocol version and '000' the service counter.

As mentioned above, the process steps 'U-D-M-S-W' are required to describe the work cycle completely. These are then stored in binary form in the data memory 9 in this order, wherein '1' describes a complete or successfully executed process step and '0' an incomplete or unsuccessfully executed process step. In order to achieve a distinction from previous cycles, the cycle count is preceded by a further '0' as a delimitation datum, which is deleted again during a subsequent conversion described in more detail below.

The data are thus stored in the data memory 9 in an optimized manner, as shown below by way of example:

| | |
|---|---|
| GA861 00001345 001 000 01 | ultrasonic cleaning performed |
| GA861 00001345 001 000 011 | cleaning and disinfection performed |
| GA861 00001345 001 000 0111 | maintenance performed |
| GA861 00001345 001 000 01111 | sterilization performed |
| GA861 00001345 001 000 011111 | working with the medical product 2 |

Exactly one bit is required for each process step.

If the data were to be stored as ascii characters, as is conventionally the case, i.e. as a sequence of the letter symbols U-D-M-S-W, this would require 6*8 bits, i.e. 48 bits. This is not acceptable due to the limited storage capacity of the data memory 9.

In order to make even better use of the available storage capacity of the data memory 9, a completely executed work cycle is stored as a binary '1'. This means that only 1 bit is required for a completely executed work cycle. As explained below by way of example, a completely executed work cycle, i.e. a sequence '011111', is converted/combined and stored as a singular '1'. In other words, in the case of a completely executed work cycle, the sequence '011111' (U-D-M-S-W) is converted into a '1' and this is stored in the data memory 9. In this context, the aforementioned delimitation datum is also deleted.

After complete and successful performance of a work cycle, the data chain is as follows:

GA861 00001345 001 000 1

It should be mentioned here that the work cycle (U-D-M-S-W) can, of course, also be extended as desired to include further process steps, such as a test run (T) in a reprocessing unit for medical devices (RUMED). Then a completely executed work cycle would look as follows: U-D-M-T-S-W ('0111111'). This change would also lead to the unique generation of a new protocol version to which a product is assigned, so that, as mentioned above, the structure of the data chain can be traced at any time on the basis of the protocol version.

However, an incomplete work cycle is not summarized or converted and therefore remains binary coded, i.e. as a sequence of binary characters, preceded by '0' in the data memory 9. If a process step, e.g. maintenance M due to forgotten oiling, is not or only insufficiently performed, the data chain in the data memory 9 is as follows:

GA861 00001345 001 000 011011 (U-D-S-W)

The successfully executed process steps U, D, S, W are stored as '1', whereas the maintenance step M that was not executed is stored as '0'.

The detection of each cycle is generated as a data chain. For example:

GA861 00001345 001 000 1111111UDSW11111DSW111DSW111111

GA861 00001345 001 000 11111110110111111100101111110010111111

In the example shown above, it can be seen that three incomplete, faulty work cycles were performed. In the first faulty cycle, the process step maintenance M is missing, and in the second and third, the process steps ultrasonic cleaning U and maintenance M. Accordingly, the first faulty work cycle is stored as sequence '011011' and the second and third faulty work cycles are each stored as the sequence '001011'. In this way, it can be clearly determined when a faulty work cycle was performed. In order to avoid further faulty work cycles, a medical technician or quality management representative can therefore intervene and, if necessary, train the hospital staff.

After a predefined interval and/or during maintenance and/or when the data memory 9 is full, the data memory 9 is emptied, i.e. the data stored in the data memory 9 are transferred/loaded to an external storage medium, e.g. an internal memory of the holding device 1 or a smartphone, where it can be further processed if necessary and can be transferred to an external network, e.g. a hospital network or a cloud server. After such a data transfer, the service counter is incremented and this is communicated to the manufacturer. In this way, it can be clearly determined at any time how many reprocessing or work cycles the medical product 2 has undergone in total.

Furthermore, as mentioned above, the data chain may additionally contain the GTIN. The GTIN is structured, for example, as follows:

0 40 38653 26855 9

That is, in the preferred embodiment, the GTIN is composed of a sequence of numbers with 14 digits. The GTIN has a preceding filling digit '0', a two-digit, preceding country identifier '40', a business identification number '38653', the item number '26855', and a control digit '9'. In the above example, the business identification number and the item number each have five digits. Alternatively, the business identification number may have six or seven digits and the item number may have four or three digits.

In the above-mentioned example, the data chain consists of the item number, the serial number, the protocol version, the service counter and (optionally) the GTIN. However, the sequence/order of the individual components of the data chain can of course be varied as desired. I.e. the order of the individual components of the data chain is freely selectable. For example, the protocol version may also be placed in front.

In addition, the number of characters of the individual components/information blocks of the data chain, i.e. the item number, the serial number, the protocol version, service counter or GTIN can be changed/fixed as required. The protocol version is responsible for controlling the content and number of characters of the individual information blocks.

In the example described above, the cycle information is detected in binary form, wherein '1' describes a successfully executed process step and '0' an unsuccessfully executed process step. Of course, it is also possible to execute the binary coding negated, i.e. a successfully executed process step is stored with '0' and an unsuccessfully executed process step is stored with '1'. Accordingly, a new cycle is also preceded by a '1' and a completely and successfully executed work cycle is converted to '0' and thus stored in the data memory 9.

The data are thus negated and stored in the data memory 9 in an optimized manner, as exemplified below:

| | |
|---|---|
| GA861 00001345 001 000 10 | ultrasonic cleaning performed |
| GA861 00001345 001 000 100 | cleaning and disinfection performed |
| GA861 00001345 001 000 1000 | maintenance performed |
| GA861 00001345 001 000 10000 | sterilization performed |
| GA861 00001345 001 000 100000 | working with the product |

With the method according to the invention for detecting and documenting the work cycles, as explained above, a larger number of work cycles can be counted and stored in relation to the product. From calculations of the applicant it became clear that with storing of the work-cycle information (U-D-M-S-W) in Ascii format, only 38 cycles can be stored in a conventionally used data memory 9 with 1664 bits.

However, if the work cycles are documented using the method of the present disclosure, in the event that there is no incomplete process step, i.e. all work cycles have been successfully and completely performed, 1544 work cycles can be recorded before the storage capacity of the data memory 9 is exhausted. In the event that 50% of the storage capacity of data memory 9 is occupied by incomplete work cycles, 752 complete work cycles and 125 incomplete cycles can still be recorded. With a 50%-50% distribution between complete and incomplete work cycles, i.e. every second work cycle is incomplete, a total of approx. 420 work cycles can be recorded, whereby 86% of the storage capacity of the data memory 9 is occupied by incomplete work cycles.

The invention claimed is:

1. A method for detecting and documenting a work cycle of a sterilizable medical product, which communicates with an external data-processing device, the method comprising the steps of:
   detecting at least one process step of the work cycle as a function of an output signal of at least one sensor;
   processing the output signal to form cycle information by the data-processing device; and
   storing the cycle information in a data chain stored in a data memory of the medical product,
   the cycle information being stored with exactly one bit in the data chain.

2. The method according to claim 1, wherein the at least one of the process step comprises at least one of:
   manual or mechanical pre-cleaning,
   cleaning and disinfection,
   maintenance,
   sterilization, and
   working with the medical product.

3. The method according to claim 1, wherein a plurality of work cycles is stored in the data memory and a bit is arranged for delimiting successive work cycles.

4. The method according to claim 1, wherein the data chain further comprises data for identifying the medical product.

5. The method according to claim 1, wherein the data chain further comprises data for defining a structure of the data chain.

6. The method according to claim 1, wherein the data chain further comprises data for determining a maintenance interval.

7. The method according to claim 1, wherein a successfully executed process step is stored as '1' and an unsuccessfully executed process step is stored as '0'.

8. The method according to claim 7, wherein a work cycle in which all process steps have been successfully performed is stored as '1'.

9. The method according to claim 1, wherein a successfully executed process step is stored as '0' and an unsuccessfully executed process step is stored as '1'.

10. The method according to claim 9, wherein a work cycle in which all process steps have been successfully performed is stored as '0'.

* * * * *